United States Patent [19]

Brooks et al.

[11] Patent Number: 5,183,818

[45] Date of Patent: Feb. 2, 1993

[54] ARYLALKYLETHER AND ARYLALKYLTHIOETHER INHIBITORS OF LIPOXYGENASE ENZYME ACTIVITY

[75] Inventors: Dee W. Brooks, Libertyville; Andrew O. Stewart, Wildwood, both of Ill.; Jonathan G. Martin, Knoxville, Tenn.

[73] Assignee: Abbott Laboratories, Abbott Park, Ill.

[21] Appl. No.: 750,362

[22] Filed: Aug. 27, 1991

[51] Int. Cl.$^5$ .................... A61K 31/38; C07D 333/32
[52] U.S. Cl. ...................... 514/231.5; 544/58.5; 544/146; 544/379; 549/60; 549/63; 549/64; 549/65; 549/68; 549/69; 549/71; 549/72; 549/76; 549/77; 549/50; 549/58; 549/488; 549/496; 549/481; 549/493; 514/438; 514/495; 514/448; 514/227.8; 514/255
[58] Field of Search ............... 549/61, 63, 64, 65, 549/68, 69, 71, 72, 60, 76, 77, 496, 488, 480, 487, 485; 514/438, 445, 447, 448, 471, 231.5, 227.8, 255; 544/146, 255, 379

[56] References Cited

U.S. PATENT DOCUMENTS

| | | | |
|---|---|---|---|
| 4,897,422 | 1/1990 | Summers | 514/575 |
| 5,026,729 | 6/1991 | Brooks et al. | 514/575 |

FOREIGN PATENT DOCUMENTS

| | | | |
|---|---|---|---|
| 0292699 | 11/1988 | European Pat. Off. | 514/575 |
| WO87/04152 | 7/1987 | PCT Int'l Appl. | |
| WO90/01929 | 3/1990 | PCT Int'l Appl. | |

*Primary Examiner*—Carolyn Elmore
*Assistant Examiner*—M. Russell
*Attorney, Agent, or Firm*—Dee W. Brooks; Andrew O. Stewart; Jonathan G. Martin

[57] ABSTRACT

The present invention provides compounds having the structure $$Y-Het-[Q_1]-X-[Q_2]-Z$$

which inhibit the catalytic action of lipoxygenase enzymes, particularly 5-lipoxygenase, and thereby reduce the biosynthesis of leukotrienes $B_4$, $C_4$, $D_4$, and $E_4$.

In the generic formula given above, X is oxygen or sulfur and Het is a heteroaryl group selected from the group consisting of furyl, thienyl, 2-, 3-, and 4-pyridyl, 2- and 3-benzo[b]furyl, 2- and 3-benzo[b]thienyl and thienothienyl.

Y is one or two substituents independently selected from hydrogen, hydroxy, halogen, cyano, alkyl, haloalkyl, alkoxy, alkylthio, alkoxyaryl), alkylthioaryl, arylalkoxy, arylalkylthio, aryloxy, arylthio, alkylamido, cycloalkyl, alkanoyl, alkoxycarbonyl, amino, alkylamino, dialkylamino, and the following groups wherein R, at each occurrence, is independently selected from hydrogen and alkyl of from one to six carbon atoms: —CRROR, —NRC(O)R, —NRC(O)OR, and —C(O)NRR.

The group $Q_1$ is absent or is divalent alkylene of from one to six carbon atoms, and $Q_2$ is divalent alkylene from from two to ten carbon atoms.

The group Z is $N(OR_1)COR_2$ where $R_1$ is selected from hydrogen or a pharmaceutically suitable salt. $R_2$ is selected from hydrogen; alkyl; cycloalkyl; amino; alkylamino, optionally substituted by hydroxyl, halogen, alkoxy or carboxyl; dialkylamino in which the alkyl groups are independently are optionally substituted by hydroxyl, halogen, alkoxy or carboxyl; cycloalkylamino; 2-hydroxyethylamino; N-morpholino; N-thiomorpholino; N-piperazine; N'-alkyl-N-piperazine and cyclopropylmethylamino.

7 Claims, No Drawings

ARYLALKYLETHER AND ARYLALKYLTHIOETHER INHIBITORS OF LIPOXYGENASE ENZYME ACTIVITY

TECHNICAL FIELD

This invention relates to novel compounds possessing lipoxygenase inhibitory activity and to pharmaceutical compositions containing such compounds and a method of lipoxygenase enzymes in humans and animal hosts in need of such treatment. More particularly, the present invention concerns certain substituted arylalkylether and -thioether compounds which are inhibitors of lipoxygenase enzyme activity and/or leukotriene biosynthesis and to pharmaceutical compositions containing the compounds and methods of lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-hydroperoxyeicosatetraenoic acid (5-HPETE) which can be reduced to 5-hydroxyeicosatetraenoic acid (5-HETE) or converted to leukotriene $A_4$ ($LTA_4$). This reactive leukotriene intermediate is enzymatically hydrated to leukotriene $B_4$ ($LTB_4$) or conjugated to the tripeptide glutathione to produce leukotriene $C_4$ ($LTC_4$). $LTA_4$ can also be hydrolyzed nonenzymatically to form two isomers of $LTB_4$. Successive proteolytic cleavage steps convert $LTC_4$ to leukotrienes $D_4$ and $E_4$ ($LTD_4$ and $LTE_4$). Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the belief that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides a class of ether and thioether compounds having the structure

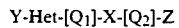

Y-Het-[Q₁]-X-[Q₂]-Z which inhibit the catalytic action of lipoxygenase enzymes, particularly 5-lipoxygenase, and thereby reduce the biosynthesis of leukotrienes $B_4$, $C_4$, $D_4$, and $E_4$.

In the generic formula given above, X is oxygen or sulfur and Het is a heteroaryl group selected from the group consisting of furyl, thienyl, 2-, 3-, and 4-pyridyl, 2- and 3-benzo[b]furyl, 2- and 3-benzo[b]thienyl and thienothienyl.

Y is one or two substituents independently selected from hydrogen, hydroxy, halogen, cyano, alkyl of from one to six carbon atoms, halogenated alkyl of from one to six carbon atoms, alkoxy of from one to six carbon atoms, alkylthio of from one to six carbon atoms, alkoxy(carbocyclic aryl) in which the alkoxy portion contains from one to six carbon atoms, alkylthio(carbocyclic aryl) in which the alkylthio portion contains from one to six carbon atoms, (carbocyclic aryl)alkoxy in which the alkoxy portion contains from one to six carbon atoms, (carbocyclic aryl)alkylthio in which the alkylthio portion contains from one to six carbon atoms, (carbocyclic aryl)oxy, (carbocyclic aryl)thio, alkylamido of from one to six carbon atoms, cycloalkyl of from three to eight carbon atoms, alkanoyl of from one to six carbon atoms, alkoxycarbonyl, amino, alkylamino of from one to six carbon atoms, dialkylamino in which the two alkyl groups are independently selected from alkyl of from one to six carbon atoms, and the following groups wherein R, at each occurrence, is independently selected from hydrogen and alkyl of from one to six carbon atoms: —CRROR, —NRC(O)R, —NRC(O)OR, and —C(O)NRR.

The group $Q_1$ is absent or is divalent alkylene of from one to six carbon atoms, and $Q_2$ is divalent alkylene from two to ten carbon atoms.

The group Z is $N(OR_1)COR_2$ where $R_1$ is selected from hydrogen or a pharmaceutically suitable salt. $R_2$ is selected from hydrogen, alkyl of from one to six carbon atoms, cycloalkyl of from three to eight carbon atoms, amino, alkylamino of from one to six carbon atoms in which the alkyl group may be optionally substituted by hydroxyl, halogen, alkoxy or carboxyl; dialkylamino in which the alkyl groups are independently selected from one to six carbon atoms in which the alkyl group may be optionally substituted by hydroxyl, halogen, alkoxy or carboxyl; cycloalkylamino of from three to six carbon atoms; 2-hydroxyethylamino; N-morpholino; N-thiomorpholino; N-piperazino; N'-alkyl-N-piperazino and cyclopropylmethylamino.

In another embodiment of the present invention, there are provided pharmaceutical compositions for inhibiting lipoxygenase enzyme activity and leukotriene biosynthesis comprising a therapeutically effective amount of a compound of Formula I in combination with a pharmaceutically acceptable carrier.

In a third aspect of the present invention, there is provided a method of inhibiting 5-lipoxygenase activity in a mammal in need of such treatment comprising administering to a mammal in need of such treatment a therapeutically effective amount of a compound of Formula I.

DETAILED DESCRIPTION AND PREFERRED EMBODIMENTS

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cycopentyl, cyclohexyl, bicyclo[2.2.1]heptanyl, and bicyclo[2.2.2]octanyl.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkylene" and "divalent alkylene" denote a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkanoyl" represents an alkyl group, as defined above, attached to the parent molecular moiety through a carbonyl group. Alkanoyl groups are exemplified by acetyl, propionyl, butanoyl and the like.

"Alkanoylamino" refers to an alkanoyl group, as defined above, attached to the parent molecular moiety through an amino group and is represented by such groups as acetylamino, propionylamino, and the like.

The term "alkoxycarbonyl" represents an ester group; i.e. an alkoxy group, attached to the parent molecular moiety through a carbonyl group such as methoxycarbonyl, ethoxycarbonyl, and the like.

The term "carbocyclic aryl" denotes a monovalent carbocyclic ring group derived by the removal of a single hydrogen atom from a monocyclic or bicyclic fused or non-fused ring system obeying the "4n+2π electron" or Huckel aromaticity rule. Examples of carbocyclic aryl groups include phenyl, 1- and 2-naphthyl, phananthryl, anthracyl, biphenylyl and the like.

The term "(carbocyclic aryl)alkyl" refers to a carbocyclic ring group as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moiety through a sulfur atom and thence through an alkylene group and are typified by phenylthiomethyl, 1- and 2-naphthylthioethyl and the like.

The term "cleavable group" denotes a group which is readily cleaved to yield the parent molecule of the structural formulae indicated above wherein M is hydrogen. Examples of cleavable groups include —COR, —COOR, —CONRR and —CH$_2$OR radicals where R is selected independently at each occurrence from alkyl, trialkylsilyl, phenyldialkylsilyl, diphenylalkylsilyl, carbocyclic aryl or carbocyclic aryl substituted with one or more of C$_1$-C$_4$ alkyl, halogen, hydroxy or C$_1$-C$_4$ alkoxy. Specific examples of representative metabolically cleavable groups include acetyl, methoxycarbonyl, benzoyl, methoxymethyl and trimethylsilyl groups.

Preferred compounds of the present invention include those in which X is oxygen and Het is 2- or 3-furyl, 2- or 3-thienyl, and 2- or 3-benzo[b]thienyl.

Compounds contemplated as falling within the scope of the present invention include, but are not necessarily limited to the followed:

N-[2-(1-(fur-2-yl)methoxy)propyl]-N-Hydroxy urea.

N-Hydroxy-N-[2-(1-[1-(5-methylfur-2-yl)]ethoxy)ethyl] urea.

N-Hydroxy-N-[2-(1-(5-methylfur-2-yl)methoxy)propyl] urea.

N-Hydroxy-N-[2-(5-methylfur-2-ylmethoxy)ethyl] urea.

N-Hydroxy-N-[2-(1-[1-(5-methylfur-2-yl)]ethoxy)propyl] urea.

N-Hydroxy-N-[2-(1-(2,5-dimethylfur-3-yl)methoxy)propyl] urea.

N-Hydroxy-N-[2-(1-(2,5-dimethylfur-3-yl)methoxy)ethyl] urea.

N-Hydroxy-N-[2-(1-(2-methylfur-3-yl)methoxy)propyl] urea.

N-Hydroxy-N-[2-(1-[1-(fur-2-yl)ethoxy)]propyl] urea.

N-hydroxy-N-[2-(5-(2-phenylethenyl)fur-2-ylmethoxy)ethyl] urea

N-[2-(1-(fur-2-yl)methylthio)propyl]-N-hydroxy urea

N-hydroxy-N-[2-(5-phenylfur-2-ylmethoxy)ethyl] urea

N-hydroxy-N-[2-(5-(4-chlorophenyl)fur-2-ylmethoxy)ethyl] urea

N-hydroxy-N-[2-(5-(4-methylphenyl)fur-2-ylmethoxy)ethyl] urea

N-Hydroxy-N-[2-(1-(5-N,N-dimethylaminomethyl)fur-2-ylmethylthio)propyl]-N'-methyl urea.

N-Hydroxy-N-[2-(fur-2-ylmethoxy)ethyl] urea.

N-Hydroxy-N-[2-(fur-3-ylmethoxy)ethyl]urea.

N-Hydroxy-N-[2-(1-(fur-3-yl)methoxy)propyl] urea.

N-Hydroxy-N-[2-(1-(5-methylthien-2-yl)methoxy)propyl] urea.

N-Hydroxy-N-[2-(1-(5-methylthien-2-yl)methoxy)ethyl] urea.
N-Hydroxy-N-[2-(thien-2-ylmethoxy)ethyl] urea.
N-Hydroxy-N-[2-(thien-2-ylmethoxy)propyl]urea.
N-Hydroxy-N-[2-(1-(thien-3-yl)methoxy)propyl] urea.
N-Hydroxy-N-[2-(thien-3-ylmethoxy)ethyl] urea.
N-Hydroxy-N-[2-(1-[(5-tert butylthio)thien-2-yl]methoxy)ethyl]urea.
N-hydroxy-N-[2-(thien-2-ylmethoxy)ethyl]acetamide
N-hydroxy-N-[2-(thien-2-ylmethoxy)ethyl]-N'-methyl urea
N-hydroxy-N-[2-(thien-2-ylmethoxy)ethyl]-N'-butyl urea
N-hydroxy-N-[2-(thien-2-ylmethoxy)ethyl]-N'-benzyl urea
N-hydroxy-N-[2-(thien-2-ylmethoxy)ethyl]-N'-phenyl urea
N-hydroxy-N-[2-(thien-2-ylmethoxy)ethyl]-N'-hydroxyethyl urea
N-hydroxy-N-[2-(thien-2-ylmethoxy)ethyl] N'-1-(4-carbomethoxyhexyl) urea
N-hydroxy-N-[2-(thien-2-ylmethoxy)ethyl] N'N'-dimethyl urea
N-hydroxy-N-[2-(thien-2-ylmethoxy)ethyl] N'-morpholinyl urea
N-hydroxy-N-[2-(thien-2-ylmethoxy)ethyl] N'-(N''-methyl)piperazinyl urea
N-hydroxy-N-[2-(5-(phenylthio)thien-2-ylmethoxy)ethyl] urea
N-hydroxy-N-[2-(5-(4-chlorophenylthio)thien-2-ylmethoxy)ethyl] urea
N-hydroxy-N-[2-(3-(phenylthio)thien-2-ylmethoxy)ethyl] urea
N-hydroxy-N-[2-(3-(4-bromophenylthio)thien-2-ylmethoxy)ethyl] urea
N-hydroxy-N-[2-(5-thiomethoxythien-2-ylmethoxy)ethyl] urea
N-hydroxy-N-[2-(3-thiomethoxythien-2-ylmethoxy)ethyl] urea
N-hydroxy-N-[2-(5-phenylthien-2-ylmethoxy)ethyl] urea
N-hydroxy-N-[2-(5-(4-chlorophenyl)thien-2-ylmethoxy)ethyl] urea
N-hydroxy-N-[2-(5-(4-methylphenyl)thien-2-ylmethoxy)ethyl] urea
N-hydroxy-N-[2-(5-(2-phenylethenyl)thien-2-ylmethoxy)ethyl] urea
N-hydroxy-N-[2-(thieno[2,3-b]thien-2-ylmethoxy)ethyl] urea
N-hydroxy-N-[2-(thieno[3,2-b]thien-2-ylmethoxy)ethyl] urea
N-Hydroxy-N-[2-(1-[1-(benzo[b]thien-2-yl)]ethoxy)ethyl) urea.
N-Hydroxy-N-[2-(1-(benzo[b]thien-2-yl)methoxy)ethyl] urea.
N-Hydroxy-N-[2-(1-(benzo[b]thien-2-yl)methoxy)propyl] urea.
N-hydroxy-N-[2-(1-(2-pyridyl)thio)propyl] urea
and compounds having the names above wherein the N-hydroxy hydrogen atom is replaced by a pharmaceutically acceptable cation, or a pharmaceutically acceptable cleavable group, as defined above.

Certain compounds of this invention may exist in stereoisomeric forms by virtue of the presence of one or more chiral centers. The present invention contemplates all such stereoisomers, including R- and S-enantiomers, diastereomers, and mixtures thereof as falling within the scope of the invention. In a particular enantiomer is desired, it may be prepared by chiral synthesis or by derivatization with a chiral auxiliary where the resulting diastereomeric mixture is separated and the auxiliary group cleaved to provide the pure desired enantiomers. Alternatively, where the molecule contains a basic functional group such as amino or an acidic functional group such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

Certain compounds of the present invention contain a basic functional group such as amino, alkylamino, or dialkylamino and are thus capable of forming salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. (See, for example S. M. Berge, et al., "Pharmaceutical Salts," *J. Pharm. Sci.*, 66: 1–19 (1977) which is incorporated herein by reference.)

In other cases, the compounds contain one or more acidic functional groups such as carboxyl and the like and are capable of forming salts with pharmaceutically acceptable bases. The term "pharmaceutically acceptable salts" in these instances refers to the relatively non-toxic, inorganic and organic base addition salts of compounds of the present invention. These salts can be likewise prepared in situ during the final isolation and purification of the compounds or by separately reacting the purified compound in its free acid form with a suitable base such as the hydroxide, carbonate or bicarbonate of a pharmaceutically acceptable metal cation or with ammonia, or an organic primary, secondary, or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine, and the like. (See, for example S. M. Berge, et al., "Pharmaceutical Salts," *J. Pharm. Sci.*, 66: 1–19 (1977) which is incorporated herein by reference.)

SYNTHESIS OF COMPOUNDS

Compounds of this invention can be prepared by the following processes. In certain cases where the intermediates contain functional groups which might interfere with the desired transformation outlined in the following schemes, it is recognized that methods of protection of these functional groups followed by deprotection at a later stage in the preparation of the desired products can be applied. A general reference source for methods of protection and deprotection is T. W. Green, "Protective Groups in Organic Synthesis", Wiley-Interscience, New York, 1981.

One process to access compounds of this invention is outlined in Reaction Scheme 1. Reaction of a arylalkylthiol I with chloroacetone provides the intermediate arylalkylthioalkylketone II which is subsequently converted to the corresponding hydroxylamine IV by known methods. The hydroxylamine intermediate IV is then converted to the desired product hydroxyurea V or hydroxamic acid VI.

Another process to acess compounds of this invention is outlined in Reaction Scheme 2. This process involves the reaction of an arylalkyl thiol or alcohol I with 1-bromo-2,3-epoxypropane (epibromohydrin) to provide the intermediate arylalkylheteroalkylepoxide II. Reduction of the epoxide function with lithium aluminum hydride provides the hydroxy intermediate III which is oxidized to the ketone intermediate IV and converted to the corresponding hydroxylamine VI by known methods. The hydroxylamine intermediate VI is then converted to the desired product hydroxyurea VII or hydroxamic acid VIII.

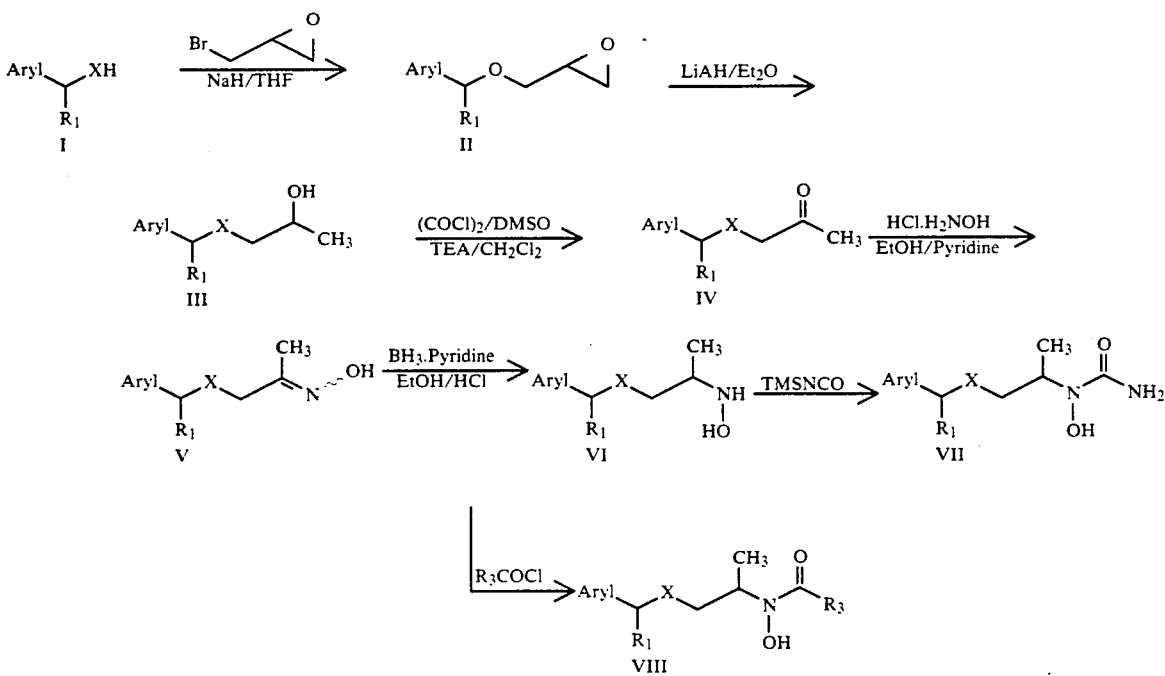

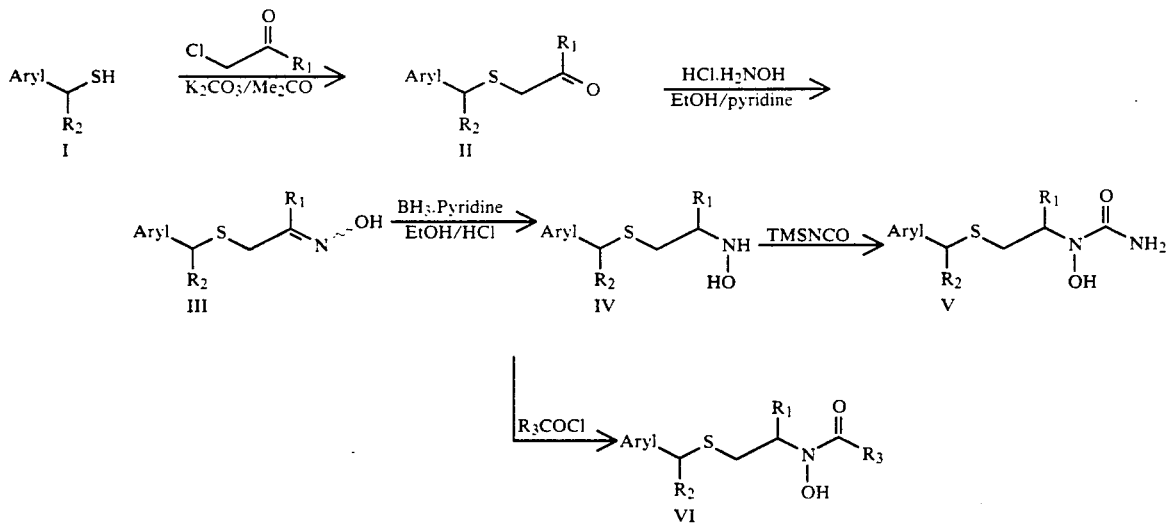

Another process to access compounds of this invention is outlined in Reaction Scheme 3. This process involves the reaction of an arylalkyl thiol or alcohol I with the iodo oxime derivative II to provide the intermediate arylalkylheteroalkyloxime derivative III. Reduction of this silyloxime derivative III provides the hydroxylamine intermediate IV. The hydroxylamine intermediate IV is then converted to the desired product hydroxyurea V or hydroxamic acid VI.

Reaction Scheme 3

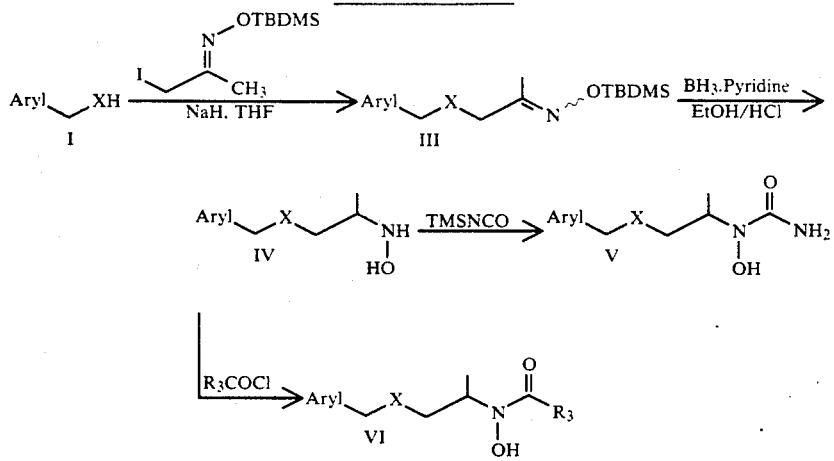

Another process to access compounds of this invention is outlined in Reaction Scheme 4. This process involves the reaction of an arylalkyl thiol or alcohol I with 1-chloroacetic acid to provide the intermediate arylalkylheteroacetic acid intermediate II which is readily converted to the corresponding hydroxamate intermediate III. This intermediate III can be converted to the aldehyde IV or to the ketone VI by known methods. These carbonyl intermediates IV and V can be converted to the desired N-hydroxyureas by the procedures previously described.

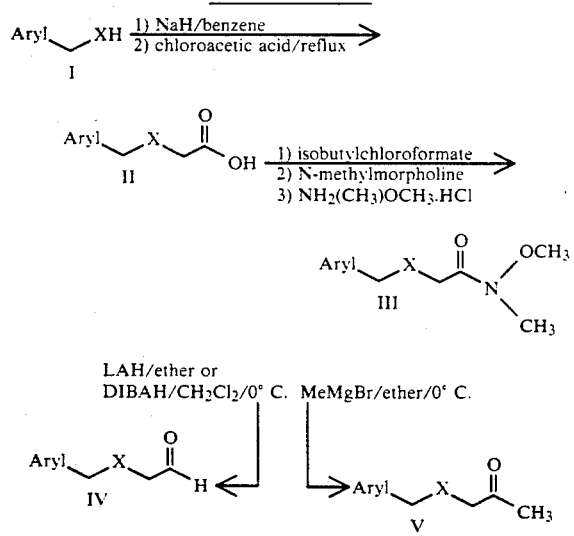

PHARMACEUTICAL COMPOSITIONS

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

The following preparative Examples are provided to enable one skilled in the art to practice the present invention. The Examples are merely illustrative of the invention, however, and are not to be read as limiting the scope of the invention as it is defined by the appended claims.

EXAMPLE 1

Preparation of
N-[2-(1-(fur-2-yl)methylthio)propyl]-N-hydroxy urea

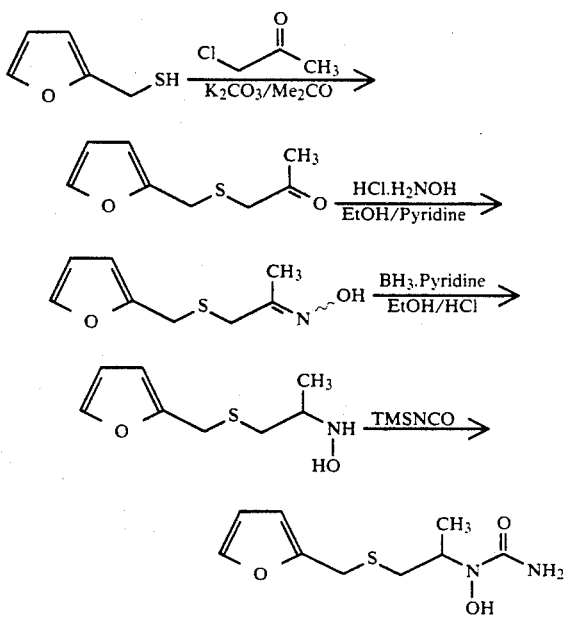

To a stirred solution of furfurylmercaptan (2.26 g, 19.83 mmol) and chloroacetone (2.20 g, 23.8 mmol) in acetone (50 mL) was added powdered potassium carbonate (3.01 g, 21.81 mmol). The mixture was heated to 40° C. for 1 h and then allowed to cool to room temperature. The resulting mixture was filtered and concentrated. The residue was dissolved in ether (150 mL), washed with water (2×50 mL) and dried (MgSO$_4$). After filtration, concentration afforded the ketone intermediate (3.0 g) as a yellow liquid that was used without further purification for subsequent oxime formation.

The ketone obtained above was dissolved in 1:1 pyridine, ethanol (50 mL). To this stirred solution was added hydroxylamine hydrochloride (3.0 g, 43 mmol). The solution was allowed to stir at room temperature overnight and then concentrated. The residue was partitioned between Et$_2$O (200 mL) and cold 3N HCl (100 mL). The organic layer was rewashed with cold 3N HCl (2×100 mL), water (2×100 mL), and dried (MgSO$_4$). Concentration afforded the oxime intermediate (3.17 g) as a yellow liquid (86%, 2 steps).

The oxime obtained above (3.17 g, 17.13 mmol) was dissolved in ethanol (50 mL) and borane pyridine (3.98 g, 42.84 mmol) was added via syringe. The reaction flask was equipped with a dropping funnel and charged with 6N HCl (20 mL). The HCl solution was added dropwise at a rate to maintain a gentle reflux. The solution was allowed to stir 1 h at room temperature and concentrated. The resulting reside was neutralized with 3N NaOH, and extracted with ethylacetate (2×100 mL). The combined organics were washed with water (1×100 mL) and dried (MgSO$_4$). Concentration afforded the hydroxylamine intermediate (2.3 g) as an off white solid (72%).

To a stirred THF (75 mL) solution of hydroxylamine obtained above (2.3 g, 12.3 mmol) was added trimethysilylisocyanate (2.12 g, 18.45 mmol). The solution was stirred for 1 h at room temperature, concentrated to approximately one half volume and poured into sat'd. NH$_4$Cl/ice. The mixture was extracted with ethyl acetate and the combined organics were washed with water (1×100 mL) and dried (MgSO$_4$). Concentration gave a residue that solidified on trituration with ether/hexanes (1:1). The solid (1.95 g) was collected and after two recrystalizations (EtOAc/hexanes) afforded the title compound as a white solid (1.7 g, 60%). m.p. 86°-87.5° C.; NMR (300 MHz, DMSO-d$_6$) δ1.06 (3H, d, J=7 Hz), 2.39 (1H, dd), 2.58 (1H, dd), 3.75 (2H, m), 4.25 (1H, m), 6.26 (1H, m), 6.30 (2H, bs), 6.38 (1H, m), 7.75 (1H, m), 8.98 (1H, s); MS m/e 248 (M+NH$_4$)$^+$, 231 (M+H)$^+$.

EXAMPLE 2

Preparation of
N-hydroxy-N-[2-(1-(2-pyridyl)thio)propyl] urea

The title compound was prepared according to the method of Example 1 except using 2-mercaptopyridine instead of furfurylmercaptan. m.p. 122°-123.5° C.; NMR (300 MHz, DMSO-d$_6$) δ1.11 (3H, d, J=7 Hz), 3.15 (1H, dd), 3.27 (1H, dd), 4.40 (1H, m), 6.32 (2H, bs), 7.10 (1H, m), 7.30 (1H, m), 7.63 (1H, m), 8.42 (1H, m), 9.13 (1H, s); MS m/e 228(M+H$^+$.

EXAMPLE 3

Preparation of
N-[2-(1-(fur-2-yl)methoxy)propyl]-N-Hydroxy urea

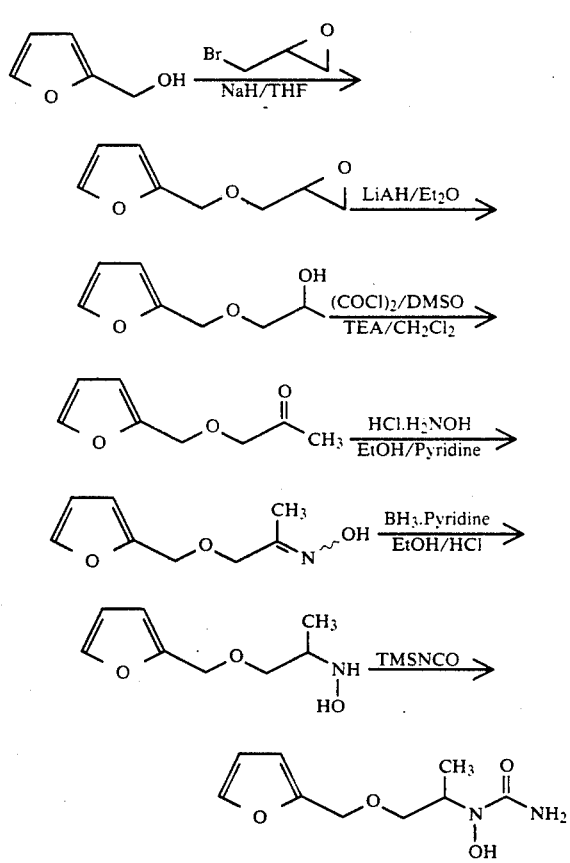

To a stirred THF (25 mL) suspension of hexane washed sodium hydride (2.97 g, 74.5 mmol) cooled to 0° C. was added a THF solution (10 mL) of furfuryl alcohol (6.65 g, 67.7 mmol). The ice bath was removed and the mixture was stirred at room temperature for 2 h.

The reaction was cooled to 0° C. and epibromohydrin (10.2 g, 74.5 mmol) was added as a THF solution (10 mL). The reaction was stirred an additional 3 h at room temperature. A small amount of water was cautiously added and the mixture concentrated. The residue was dissolved in ether (250 mL), washed with water (2×100 mL) and dried (MgSO4). Concentration and purification by chromatography (silica gel, 10% EtOAc/hexanes) afforded 7.37 g (71%) of the desired epoxide intermediate as a yellow liquid.

To a 0° C. stirred ether (100 mL) suspension of lithium aluminum hydride (1.81 g, 47.86 mmol) was added an ether (50 mL) solution of the epoxide (7.37 g, 47.86 mmol) via an addition funnel. The reaction was allowed to stir for 1 h and sodium sulfate decahydrate was added very cautiously. A large excess of sodium sulfate decahydrate was then added and the mixture was allowed to stir overnight. The solution was filtered and concentrated to afford 7.12 g (95%) of the hydroxy intermediate.

To a −78° C. stirred methylene chloride (100 mL) solution of oxalylchloride (6.95 g, 54.8 mmol) was added DMSO (8.55 g, 109.5 mmol). After 0.25 h a methylene chloride solution of the alcohol obtained above (7.12 g, 45.64 mmol) was added and the mixture was stirred at −78° C. for an additional 0.5 h. Triethylamine (23.1 g, 228.2 mmol) was added to the reaction mixture via syringe and the ice bath removed. The reaction was stirred 1 h at room temperature and concentrated to dryness. The residue was dissolved in THF and filtered. The solution was concentrated and purified by chromatography (silica gel, 33% EtOAc/hexanes) to afford 6.4 g (91%) of the ketone intermediate.

The title compound was prepared from this ketone intermediate according to the procedures used for oxime formation, reduction to the hydroxylamine and N-hydroxyurea formation as described for Example 1. m.p. 59°-62° C.; NMR (300 MHz, DMSO-d6) δ0.96 (3H, d, J=6 Hz), 3.42 (1H, m), 3.46 (1H, m), 4.27 (1H, m), 4.39 (2H, s), 6.26 (2H, bs), 7.63 (1H, m), 8.95 (1H, s); MS m/e 232 (M+NH4)+, 215 (M+H)+.

EXAMPLE 4

Preparation of
N-Hydroxy-N-[2-(1-[1-(5-methylfur-2-yl)]ethoxy)ethyl] urea

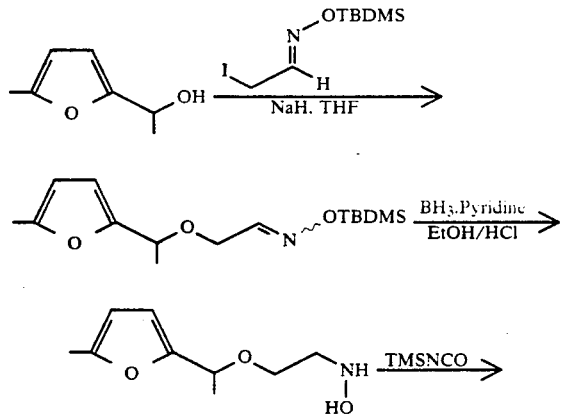

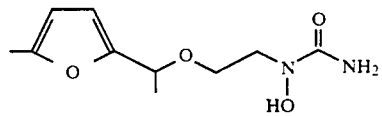

Preparation of iodoacetaldehyde O-t-butyldimethylsilyloxime. In a 500 mL roundbottom flask were combined water (25 mL) and 50 mL of 50% aqueous chloroacetaldehyde solution (~319 mmol) and hydroxylamine hydrochloride (27.5 g, 399 mmol) was added as a solid. The reaction was allowed to stir for 1 h at 0° C., poured into water (100 mL) and extracted with EtOAc (2×150 mL). The combined organics were washed with water until the wash was neutral (pH~5). The organics were dried (MgSO4) and concentrated to afford 23.7 g of the chloroacetaldehyde oxime as a slightly yellow oil (80%).

The oxime obtained above (23.7 g, 254 mmol) was placed in a 500 mL roundbottom flask under argon and cooled to 0° C. Tert-butyldimethylchlorosilane (45.9 g, 304 mmol) was added followed by the addition of pyridine (150 mL). The resulting solution was stirred at 0° C. for 1 h and then stored at −5° C. overnight. The solution was poured onto ice/water and extracted with ether (2×150 ml). The combined organic layer was washed with cold 5% HCl until the wash was acidic (pH~1). The organic layer was washed with water (2×100 mL), dried (MgSO4) and concentrated. The resulting residue was purified by chromatography (silica gel, hexane) to afford 25.2 g of the O-silyl-α-chloro oxime as a clear oil (48%).

To a stirred acetone (15 mL) solution of the O-silyl-α-chloro oxime (1.5 g, 7.23 mmol) obtained above was added NaI (1.63 g, 10.85 mmol). The solution was heated to reflux for 15 min., cooled, filtered and concentrated. The resulting residue was dissolved in ether and washed with dilute sodium thiosulfate, water and dried (MgSO4). Concentration gave the crude α-iodo-oxime intermediate that was used without further purification.

To a stirred THF (30 mL) suspension of pentane washed NaH (0.278 g, 11.6 mmol) at 0° C. under nitrogen was added a THF (5 mL) solution of 2-(1-hydroxyethyl)-5-methylfuran. The reaction mixture was stirred for 45 min. and the iodoacetaldehyde oxime (4.52 g, 14.5 mmol) was added dropwise. The solution was warmed to room temperature and allowed to stir overnight. The solvent was removed in-vacuo and the residue was diluted with ether. The ethereal layer was washed with water (2×25 mL) dried over MgSO4 and concentrated to provide a 21% yield of intermediate oxime after chromatography (silica gel, 3% ether/hexanes).

To a stirred THF:AcOH (2:1) solution of the oxime obtained above (0.59 g, 2 mmol) was added NaBH3CN (0.125 g, 2 mmol). The reaction was stirred overnight. The following day the solvent was removed in-vacuo and the residue was diluted with water (20 mL) and neutralized with 2N NaOH. The aqueous mixture was extracted with ethyl acetate (3×25 mL). The organic layers were combined, dried over MgSO4, and evaporated. The oily residue was used without further purification.

The hydroxy urea was obtained as in Example 1 using the hydroxylamine described above and was purified by chromatography (silica gel, 7% MeOH/CH2Cl2) to afford title compound as a clear oil (10% based on the starting oxime). NMR (300 MHz, DMSO-d$_6$) δ1.36 (3H, d, J=7.5 Hz), 2.24 (3H, S), 3.37 (4H, m), 4.42 (1H, q, J=7.5 Hz), 5.99 (1H, m), 6.24 (3H, m), 9.30 (1H, s); MS m/e (DCI-NH3) 246 (M+NH4)$^+$, 229(M+H).

EXAMPLE 5

Preparation of
N-Hydroxy-N-[2-(1-(5-methylfur-2-yl)methoxy)propyl] urea

Iodoacetone O-t-butyldimethylsilyloxime was prepared in a same manner as described for Example 4 except using chloroacetone instead of chloroacetaldehyde.

To a stirred THF (30 mL) suspension of pentane washed NaH (0.278 g, 11.6 mmol) at 0° C. under nitrogen was added a THF (5 mL) solution of 2-hydroxymethyl-5-methylfuran. The reaction mixture was stirred for 45 minutes and the iodoacetone oxime from above (4.52 g, 14.5 mmol) was added dropwise. The solution was warmed to room temperature and allowed to stir overnight. The solvent was removed in-vacuo and the residue was diluted with ether. The ethereal layer was washed with water (2×25 mL) dried over MgSO4 and concentrated. The oxime intermediate was purified by chromatography (silica gel, 3% ether/hexane).

To a stirred ethanol (40 mL) solution of the oxime intermediate (1.4 g, 4.6 mmol) obtained above was added BH$_3$.Pru (1.2 mL, 11.6 mmol). The reaction mixture was stirred for 20 min and then 10% HCl (12 mL) was added dropwise. After stirring for 3 h the reaction was neutralized with 2N NaOH and the ethanol was evaporated at reduced pressure. The residue was diluted with water (75 mL) and extracted with EtOAc (3×50 mL). The organic layers were combined and dried over MgSO$_4$. The solvent was removed to afford a yellow oil. The hydroxylamine was used without further purification.

The hydroxyurea was obtained as in Example 1 using the hydroxylamine described above and was purified by chromatography (silica gel, 7% MeOH/CH$_2$Cl$_2$). A 16% yield was obtained based on the starting oxime. m.p. 81°–82° C.; NMR (300 MHz, DMSO-d$_6$) δ0.96 (3H, m), 2.24 (3H, S), 3.22 (1H, m), 3.44 (1H, m), 4.25 (1H, m), 4.32 (2H, s), 6.01 (1H, m), 6.26 (3H, m), 8.94 (1H, s); MS m/e (DCI-NH3) 246 (M+NH$_4$)$^+$, 229(M+H)$^+$.

EXAMPLE 6

Preparation of
N-Hydroxy-N-[2-(5-methylfur-2-ylmethoxy)ethyl] urea

The desired product was prepared according to the method of Example 4 using 2-hydroxymethyl-5-methylfuran instead of 2-(2-hydroxyethyl)-5-methylfuran. The desired product was purified by chromatography (silica gel, 7% MeOH/CH$_2$Cl$_2$) to afford title compound as a white solid (21%). m.p. 67°–68° C.; NMR (300 MHz, DMSO-d$_6$) δ2.25 (3H, s), 3.49 (4H, m), 4.33 (2H, s), 6.02 (1H, m), 6.27 (3H, m), 9.33 (1H, s); MS m/e (DCI-NH3) 232 (M+NH4)$^+$, 215(M+H)$^+$.

EXAMPLE 7

Preparation of
N-Hydroxy-N-[2-(1-[1-(5-methylfur-2-yl)]ethoxy)propyl] urea

The desired product was prepared according to the method of Example 5 using 2-(1-hydroxyethyl)-5-methylfuran instead of 2-hydroxymethyl-5-methylfuran. The desired product was purified by chromatography (silica gel, 7% MeOH/CH$_2$Cl$_2$) to afford a clear oil (12% based on the starting oxime). NMR (300 MHz, DMSO-d$_6$) δ0.93 (3H, d, J=7.5 Hz), 1.36 (3H, d, J=7.5 Hz), 2.24 (3H, S), 3.15 (1H, m), 3.37 (2H, m), 4.42 (1H, q, J=7.5 Hz), 5.99 (1H, m), 6.24 (3H, m), 9.30 (1H, s); MS m/e (DCI-NH3) 260(M+NH4)+, 243 (M+H)$^+$.

EXAMPLE 8

Preparation of
N-Hydroxy-N-[2-(1-(2,5-dimethylfur-3-yl)methoxy)propyl] urea

The desired product was prepared according to the method of Example 5 using 2,5-dimethyl-3-(hydroxymethyl)furan instead of 2-hydroxymethyl-5-methylfuran. The desired product was purified by chromatography (silica gel, 7% MeOH/CH$_2$Cl$_2$) to afford a clear oil (53% based on the starting oxime). NMR (300 MHz, DMSO-d$_6$) δ0.96 (3H, d), 2.17 (6H, S), 3.17 (1H, m), 3.38 (1H, m), 4.17 (2H, s), 4.27 (1H, m), 5.94 (1H, br. s), 6.24 (2H, br.s), 8.91 (1H, s); MS m/e (DCI-NH3) 260 (M+NH4)$^+$, 243 (M+H)$^+$.

EXAMPLE 9

Preparation of
N-Hydroxy-N-[2-(1-(2,5-dimethylfur-3yl)methoxy)ethyl] urea

The desired product was prepared according to the method of Example 4 using 2,5-dimethyl-3-(hydroxymethyl)furan instead of 2-(2-hydroxyethyl)-5-methylfuran. The desired product was purified by chromatography (silica gel, 7% MeOH/CH$_2$Cl$_2$) to afford a clear oil (70% based on the starting oxime). NMR (300 MHz, DMSO-d$_6$) δ2.18 (6H, s), 3.47 (4H, m), 4.20 (2H, s), 5.94 (1H, s), 6.25 (2H, br.s), 9.29 (1H, s); MS m/e (DCI-NH3) 246 (M+NH$_4$)$^+$, 229 (M+H)$^+$.

EXAMPLE 10

Preparation of
N-Hydroxy-N-[2-(1-(2-methylfur-3-yl)methoxy)propyl] urea

The desired product was prepared according to the method of Example 5 using 2-methyl-3-(hydroxymethyl)furan instead of 2-hydroxymethyl-5-methylfuran. The desired product was purified by chromatography (silica gel, 7% MeOH/CH$_2$Cl$_2$) to afford a white solid (45% based on the starting oxime). m.p. 101°–102° C.; NMR (300 MHz, DMSO-d$_6$) δ0.96 (3H, m), 2.23 (3H, S), 3.20 (1H, m), 3.42 (1H, m), 4.26(3H, m), 6.24 (2H, br.s), 6.35 (1H, m), 7.44 (1H,m), 8.92(1H, s); MS m/e (DCI-NH3) 246 (M+NH4)$^+$, 229 (M+H)$^+$.

EXAMPLE 11

Preparation of
N-Hydroxy-N-[2-(1-(fur-3-yl)methoxy)propyl] urea

The desired product was prepared according to the method of Example 5 using 3-hydroxymethylfuran instead of 2-hydroxymethyl-5-methylfuran. The desired product was purified by chromatography (silica gel, 7% MeOH/CH$_2$Cl$_2$) to afford a white solid (37% based on starting oxime). m.p. 121.5°–122.5° C.; NMR (300 MHz, DMSO-d$_6$) δ0.98 (3H, m), 3.22 (1H, m), 3.46 (1H, m), 4.31(3H, m), 6.26 (2H, br.s), 6.48 (1H, m), 7.62 (2H, m), 8.92 (1H, s); MS m/e (DCI-NH3) 232 (M+NH4)$^+$, 215 (M+H)$^+$.

EXAMPLE 12

Preparation of N-Hydroxy-N-[2-(1-[1-(fur-2-yl)ethoxy)]propyl] urea

The desired product was prepared according to the method of Example 5 using 2-(1-hydroxyethyl)furan instead of 2-hydroxymethyl-5-methylfuran. The desired product was purified by chromatography (silica gel, 66% ethyl acetate/hexane) to afford a thick clear oil as a 1:1 mixture of diastereomers (50% based on the starting oxime). NMR (300 MHz, DMSO-$d_6$) $\delta$ 0.93 (1.5H, d, J=7.Hz), 0.97 (1.5H, d, J=7.Hz), 1.38 (3H, m), 3.13 (2H, m), 4.22 (1H, m), 4.98 (1H, m), 6.23 (1H, br. s), 6.26 (1H, br. s), 6.35 (1H, m), 6.47 (1H, m), 7.61 (1H, m), 8.91 (0.5H, s), 8.92 (0.5H, s); MS m/e (DCI-NH3) 229 (M+H)+, 186, 135.

EXAMPLE 13

Preparation of N-Hydroxy-N-[2-(1-(5-methylthien-2-yl)methoxy)propyl] urea

The desired product was prepared according to the method of Example 5 using 2-methoxy-5-methylthiophene instead of 2-hydroxymethyl-5-methylfuran. The desired product was purified by chromatography (silica gel, 7% MeOH/CH$_2$Cl$_2$) to afford a white solid (60% based on the starting oxime). m.p. 84°-85° C.; NMR (300 MHz, DMSO-$d_6$) $\delta$ 0.97 (3H, d, J=7.5 Hz), 2.41 (3H, m), 3.24(1H, m), 3.45 (1H, m), 4.27 (1H, m), 4.52 (2H, s), 6.24 (2H, br. s), 6.65 (1H, m), 6.81 (1H, m), 8.93 (1H, s); MS m/e (DCI-NH3) 262 (M+NH4)+, 245 (M+H)+.

EXAMPLE 14

Preparation of N-Hydroxy-N-[2-(1-(5-methylthien-2-yl)methoxy)ethyl] urea

The desired product was prepared according to the method of Example 4 using 2-hydroxymethyl-5-methylthiophene instead of 2-(2-hydroxyethyl)-5-methylfuran. The desired product was purified by chromatography (silica gel, 7% MeOH/CH$_2$Cl$_2$) to afford title compound as a white solid (29% based on the starting oxime). m.p. 95°-96° C.; NMR (300 MHz, DMSO-$d_6$) $\delta$ 2.42 (3H, s), 3.50 (4H, m), 4.54 (2H, s), 6.27 (2H, br. s), 6.66 (1H, m), 6.82 (1H, m), 9.41 (1H, s); MS m/e (FAB) 231 (M+H)+.

EXAMPLE 15

Preparation of N-Hydroxy-N-[2-(1-[1-(benzo[b]thien-2-yl)]ethoxy)ethyl) urea

The desired product was prepared according to the method of Example 4 using 2-(1-hydroxyethyl) benzo[b]thiophene instead of 2-(2-hydroxyethyl)-5-methylfuran. The desired product was purified by chromatography (silica gel, 7% MeOH/CH$_2$Cl$_2$) to afford a white solid (32% based on the starting oxime). m.p. 114°-115° C.; NMR (300 MHz, DMSO-$d_6$) $\delta$ 1.48 (3H, d, J=7.5 Hz), 3.50 (4H, m), 4.88 (1H, q, J=7.5 Hz), 6.28 (2H, br.s), 7.34 (3H, m), 7.79 (1H, m), 7.93 (1H, m), 9.38 (1H, s); MS m/e (DCI-NH3) 298 (M+NH4)+, 281 (M+H).

EXAMPLE 16

Preparation of N-Hydroxy-N-[2-(1-(benzo[b]thien-2-yl)methoxy)ethyl] urea

The desired product was prepared according to the method of Example 4 using 2-hydroxymethylbenzo[b]thiophene instead of 2-(2-hydroxyethyl)-5-methylfuran. The desired product was purified by precipitation from THF/hexanes to afford a white solid (74%). m.p. 115°-117° C.; NMR (300 MHz, DMSO-$d_6$) $\delta$ 3.55 (2H, m), 3.61 (2H, m), 4.77 (2H, s), 6.31 (2H, br.s), 7.30-7.40 (3H, m), 7.81 (1H, m), 7.94 (1H, m), 9.36 (1H, s); MS m/e (DCI-NH3) 284 (M+NH4), 267 (M+H)+, 224, 147.

EXAMPLE 17

Preparation of N-Hydroxy-N-[2-(1-(benzo[b]thien-2-yl)methoxy)propyl] urea

The desired product was prepared according to the method of Example 5 using 2-hydroxymethylbenzo[b]thiophene instead of 2-hydroxymethyl-5-methylfuran. m.p. 132°-133° C.; NMR (300 MHz, DMSO-$d_6$) d 0.90 (3H, d, J=7 Hz), 3.34 (1H, m), 3.55 (1H, m), 4.35 (1H, q, J=7 Hz), 4.75 (2H, s), 6.28 (2H, br.s), 7.28-7.40 (3H, m), 7.81 (1H, m), 7.93 (1H, m), 8.97 (1H, s); MS m/e (DCI-NH3) 298 (M+NH4)+, 281 (M+H)+, 238, 222, 147.

EXAMPLE 18

Preparation of N-Hydroxy-N-[2-(1-(5-N,N-dimethylaminomethyl)fur-2-ylmethylthio)-propyl]-N'-methyl urea Reaction of 1-furanylmethylmercaptan with iodoacetone O-t-butyldimethylsilyloxime according to the method for Example 5 provided the intermediate oxime ether.

To a stirred solution acetonitrile (25 mL) solution of the oxime ether (7.83 g, 26.19 mmol) obtained above was added N,N-dimethylmethylene-amonium chloride (2.94 g, 31.42 mmol). The heterogeneous mixture was allowed to stirr overnight at room temperature. The reaction was concentrated, diluted with ether (200 mL), washed with water (100 mL), and dried(MgSO$_4$). Concentration and purification by chromatography (silica gel, 2% MeOH/CH$_2$Cl$_2$) afforded 5.73 g of the 5-(N,N-dimethylaminomethyl) intermediate as a clear oil.

Oxime reduction as before resulted in a 49% yield of the desired hydroxylamine intermediate after purification by chromatography (silica gel, 89:9:1 CH$_2$Cl$_2$:MeOH:conc.NH$_4$OH).

The desired product was obtained by reaction with N-methylisocyanate; purified by chromatography (silica gel, 7% MeOH/CH$_2$Cl$_2$) to afford the title compound as an oil (23%). NMR (300 MHz, DMSO-$d_6$) $\delta$ 1.05 (3H, d, J=7 Hz), 2.13 (6H, s), 2.37 (1H, m), 2.55 (1H; m), 2.60 (3H, d, J=4 Hz), 3.35 (2H, m), 3.71 (2H, m), 4.21 (1H, q, J=7 Hz), 6.18 (2H, m), 6.85 (1H, m), 8.89 (1H, s); MS m/e (DCI-NH3) 302 (M+H)+, 245, 137, 110.

EXAMPLE 19

Preparation of
N-Hydroxy-N-[2-(thien-2-ylmethoxy)ethyl] urea

To a stirred benzene suspension of NaH (0.39 g, 32.2 mmol) was added a benzene solution of 2-hydroxymethylthiophene (2.0 g, 15.1 mmol). The reaction was stirred 3 h and a benzene solution (10 mL) of chloroacetic acid (1.56 g, 16.6 mmol) was added. The reaction was heated to reflux for 15 h then cooled to room temperature and a small amount of water was cautiously added. The aqueous layer was diluted, separated, acidified and extracted with methylene chloride (3×50 mL). The combined organic layers were dried over MgSO$_4$. Evaporation afforded thien-2-ylmethoxyacetic acid as a tan oil (66%).

To a stirred 0° C. THF(100 mL) solution of the acid obtained above, was added isobutylchloroformate (1.66 g, 12 mmol)) and N-methylmorpholine (2.3 g, 23.2 mmol). The mixture was stirred for 0.5 h and N,O-dimethylhydroxylamine hydrochloride (1.1 g, 11.0 mmol)) was added as a solid. The reaction was stirred for 12 h at room temperature. The reaction was quenched with water and extracted with ethyl acetate (3×50 mL). The organic layers were combined, dried over MgSO$_4$ and evaporated. Purification by chromatography (silica gel, 60% ether/hexane) afforded the desired hydroxamate intermediate as a clear oil (85).

To a stirred 0° C. ether (100 mL) suspension of LAH (0.56 g, 14 mmol) was added an ether solution of the hydroxamic acid intermediate (2.3 g, 23.2 mmol) obtained above. The reaction mixture was stirred for 1 h and water, 15% NaOH, water (0.6 mL: 0.6 mL: 1.8 mL) were added sequentially to the cold solution. The solids were filtered and the ether was evaporated. The crude aldehyde obtained in this manner was converted to the title compound by the method as described for Example 1 providing a white solid (5%). m.p. 91°–92° C.; NMR (300 MHz, CDCl$_3$) δ3.80 (4H, m), 4.78 (2H, s), 5.21 (2H, bs), 6.90 (1H, s), 7.00 (2H, m), 7.32 (1H, m); MS m/e (DCI-NH3) 234 (M+NH4)+, 217 (M+H)+.

EXAMPLE 20

Preparation of
N-Hydroxy-N-[2-(thien-2-ylmethoxy)propyl]urea

Methylmagnesium bromide was added an ether solution of the O-methylhydroxamic acid intermediate from Example 19. The reaction mixture was stirred for 1 h and water, 15% NaOH, and water were added sequentially to the cold solution. The solids were filtered and the ether was evaporated. The crude ketone obtained in this manner was converted to the title compound by the method used for Example 1, to afford a white solid (5%). mp 101°–102.5° C.; NMR (300 MHz, DMSO-d$_6$) δ0.98 (3H, d, J=6.5 Hz), 3.28 (1H, m), 3.49 (1H, m), 4.30 (1H, m), 4.63 (2H, m), 6.25 (2H, bs), 6.99 (1H, m), 7.04 (1H, m), 7.49(1H, m), 8.95 (1H, s); MS m/e (DCI-NH3) 248 (M+NH4)+, 231 (M+H)+.

EXAMPLE 21

Preparation of
N-Hydroxy-N-[2-(1-thien-3-yl)methoxy)propyl] urea

The desired product was prepared according to the method of Example 5 using 3-hydroxymethylthiophene instead of 2-hydroxymethyl-5-methylfuran, to afford a white solid. m.p. 117°–118° C.; NMR (300 MHz, DMSO-d$_6$) δ0.98 (3H, d, J=7 Hz), 3.25 (1H, m), 3.49 (1H, m), 4.33 (1H, m), 4.44 (2H, m), 6.26 (2H, br. s), 7.07 (1H, m), 7.38 (1H, m), 7.50 (1H, m), 8.92 (1H, s); MS m/e (DCI-NH3) 248 (M+NH4)+, 231 (M+H)+.

EXAMPLE 22

Preparation of
N-Hydroxy-N-[2-(thien-3-ylmethoxy)ethyl] urea

The title compound was prepared according to the method of Example 19 using 3-hydroxymethylthiophene instead of 2-hydroxymethylthiophene, to afford a white solid. m.p. 99°–100° C.; NMR (300 MHz, DMSO-d$_6$) δ3.53 (4H, m), 4.46 (2H, s), 6.38 (2H, br. s), 7.07 (1H, dd), 7.42 (1H, m), 7.50 (1H, dd), 9.32 (1H, s); MS m/e (DCI-NH3), 217 (M+H)+, 174.

EXAMPLE 23

Preparation of
N-Hydroxy-N-[2-(fur-3-ylmethoxy)ethyl]urea

The title compound was prepared according to the method of Example 19 using 3-hydroxymethylfuran instead of 2-hydroxymethylthiophene, to afford a white solid. m.p. 99°–101° C.; NMR (300 MHz, DMSO-d$_6$) δ3.52 (4H, m), 4.33 (2H, s), 6.28 (2H, br. s), 6.48 (1H, m), 7.63 (2H, m), 9.32 (1H, s); MS m/e (DCI-NH3) 218 (M+NH4)+, 201 (M+H)+, 185.

EXAMPLE 24

Preparation of
N-Hydroxy-N-[2-(fur-2-ylmethoxy)ethyl] urea

The title compound was prepared according to the method of Example 19 using 2-hydroxymethylfuran instead of 2-hydroxymethylthiophene, to afford a white solid, m.p. 72°–75° C.; NMR (300 MHz, DMSO-d$_6$) δ3.50 (4H, m), 4.41 (2H, s), 6.29 (2H, br. s), 6.43 (2H, m), 7.65 (1H, m), 9.43 (1H, s); MS m/e (DCI-IBU) 401 (2M+H), 201 (M+H)+, 161, 103 Anal. Calcd for C$_8$H$_{12}$N$_2$O$_4$: C, 48.0; H, 6.04; N, 13.99. Found: C, 47.93; H, 5.99; N, 13.87.

EXAMPLE 25

Preparation of N-Hydroxy-N-[2-(1-[(5-tert butylthio)thien-2-yl]methoxy)ethyl]urea 2-Hydroxymethyl-(5-tertbutylthio)thiophene was prepared by lithium aluminium hydride reduction of (5-tertbutylthio)thiophene-2-carboxaldehyde. This aldehyde was obtained by reaction of tertButylmercaptan and 5-bromothiophene-2-carboxaldehyde.

The title hydroxy urea was prepared according to the method of Example 19 using 2-hydroxymethyl-(5-tert-butylthio)thiophene instead of 2-hydroxymethylthiophene, to afford a white solid. m.p. 114°–115° C.; NMR (300 MHz, DMSO-d$_6$) δ1.26 (9H, S), 3.54 (4H, m), 4.62 (2H, s), 6.29 (2H, br. s), 7.03 (1H, m), 7.07 (1H, m), 9.32 (1H, s); MS m/e (DCI-NH3) 322 (M+NH4)+, 305 (M+H)+, 185.

EXAMPLE 26

Preparation of
N-hydroxy-N-[2-(thien-2-ylmethoxy)ethyl]acetamide

The title compound is prepared from 2-(thien-2-ylmethoxy)ethyl hydroxylamine from Example 19 by first reaction with 3 equivalents of acetyl chloride and 3.3 equivalents of triethylamine followed by treatment with LiOH in 2-propanol.

EXAMPLE 27

Preparation of
N-hydroxy-N-[2-(thien-2-ylmethoxy)ethyl]-N'-methyl urea

The title compound is prepared according to the method of Example 19, except using methyl isocyanate instead of trimethylsilyl isocyanate.

EXAMPLE 28

Preparation of
N-hydroxy-N-[2-(thien-2-ylmethoxy)ethyl]-N'-butyl urea

The title compound is prepared according to the method of Example 19, except using butyl isocyanate instead of trimethylsilyl isocyanate.

EXAMPLE 29

Preparation of
N-hydroxy-N-[2-(thien-2-ylmethoxy)ethyl]-N'-benzyl urea

The desired material is prepared according to the method of Example 19, except using benzyl isocyanate instead of trimethylsilyl isocyanate.

EXAMPLE 30

Preparation of
N-hydroxy-N-[2-(thien-2-ylmethoxy)ethyl]-N'-phenyl urea

The desired material is prepared according to the method of Example 19, except using phenyl isocyanate instead of trimethylsilyl isocyanate.

EXAMPLE 31

Preparation of
N-hydroxy-N-[2-(thien-2-ylmethoxy)ethyl]-N'-hydroxyethyl urea 2-(Thien-2-ylmethoxy)ethyl hydroxylamine from Example 19 is treated with ethyl isocyanatoacetate in THF; workup and purification by column chromatography gives N-hydroxy-N-[2-(thien-2-ylmethoxy)ethyl] N'-methylethoxycarbonyl urea which is then treated with lithium borohydride in THF at room temperature. After the reaction is complete excess borohydride is quenched with methanol and the reaction is concentrated. The resulting residue is recrystalized to give the title compound.

EXAMPLE 32

Preparation of
N-hydroxy-N-[2-(thien-2-ylmethoxy)ethyl] N'-1-(4-carbomethoxyhexyl) urea To a stirred solution of the mono-methyl ester of pimelic acid in benzene is added trithylamine and dipenylphosphoryl azide. After heating to reflux for one hour, 2-(thien-2-ylmethoxy)ethyl hydroxylamine from Example 19 is added. Workup and purification gives the title N-hydroxy urea.

EXAMPLE 33

Preparation of
N-hydroxy-N-[2-(thien-2-ylmethoxy)ethyl] N'N'-dimethyl urea 2-(Thien-2-ylmethoxy)ethyl hydroxylamine from Example 19 is treated with dimethylcarbamoyl chloride and triethylamine in methylene chloride at 0° C. Workup and purification gives the desired title N-hydroxy urea.

EXAMPLE 34

Preparation of
N-hydroxy-N-[2-(thien-2-ylmethoxy)ethyl] N'-morpholinyl urea

HCl gas is bubbled through a toluene solution of 2-(thien-2-ylmethoxy)ethyl hydroxylamine from Example 19 for about 4 min. A toluene solution of phosgene is added and the mixture is heated to reflux for 1 h. The excess phosgene and toluene are removed by distillation and the residue is dissolved in THF. This solution is cooled to 0° C. and morpholine is added. After workup the desired title compound is purified by recrystalization

EXAMPLE 35

Preparation of
N-hydroxy-N-[2-(thien-2-ylmethoxy)ethyl] N'-(N''-methyl)piperazinyl urea The title compound is prepared according to the Example 34 except using 1-methylpiperazine instead of morpholine.

EXAMPLE 36

Preparation of
N-hydroxy-N-[2-(5-(phenylthio)thien-2-ylmethoxy)ethyl] urea

2-Hydroxymethyl-(5-phenylthio)thiophene is prepared by lithium aluminium hydride reduction of (5-phenylthio)thiophene-2-carboxaldehyde. This aldehyde is obtained by reaction of thiophenol and 5-bromothiophene-2-carboxaldehyde. The title compound is prepared according to the method of Example 19 using 2-hydroxymethyl-(5-phenylthio)thiophene instead of 2-hydroxymethylthiophene.

EXAMPLE 37

Preparation of
N-hydroxy-N-[2-(5-(4-chlorophenylthio)thien-2-ylmethoxy)ethyl] urea 2-Hydroxymethyl-5-(4-chlorophenylthio)thiophene is prepared by lithium aluminium hydride reduction of 5-(4-chlorophenylthio)thiophene-2-carboxaldehyde. This aldehyde is obtained by reaction of 4-chlorothiophenoltand 5-bromothiophene-2-carboxaldehyde. The title compound is prepared according to the method of Example 19 using 2-hydroxymethyl-5-(4-chlorophenylthio)thiophene instead of 2-hydroxymethylthiophene.

EXAMPLE 38

Preparation of
N-hydroxy-N-[2-(3-(phenylthio)thien-2-ylmethoxy)ethyl] urea

2-Hydroxymethyl-(3-phenylthio)thiophene is prepared by lithium aluminium hydride reduction of (3-phenylthio)thiophene-2-carboxaldehyde. This aldehyde is obtained by reaction of thiophenol and 3-bromothiophene-2-carboxaldehyde. The title compound is prepared according to the method of Example 19 using 2-hydroxymethyl-(3-phenylthio)thiophene instead of 2-hydroxymethylthiophene.

EXAMPLE 39

Preparation of N-hydroxy-N-[2-(3-(4-bromophenylthio)thien-2-ylmethoxy)ethyl] urea 2-Hydroxymethyl-(3-(4-bromophenyl)thiophene is prepared by lithium aluminium hydride reduction of (3-(4-bromophenyl)thiophene-2-carboxaldehyde. This aldehyde is obtained by reaction of 4-bromothiophenol and 3-bromothiophene-2-carboxaldehyde. The title compound is prepared according to the method of Example 19 using 2-hydroxymethyl-(3-(4-bromophenyl)-thiophene instead of 2-hydroxymethylthiophene.

EXAMPLE 40

Preparation of N-hydroxy-N-[2-(5-thiomethoxythien-2-ylmethoxy)ethyl] urea

2-Hydroxymethyl-(5-methythio)thiophene is prepared by lithium aluminium hydride reduction of (5-methylthio)thiophene-2-carboxaldehyde. This aldehyde is obtained by reaction of methylmercaptan and 5-bromothiophene-2-carboxaldehyde. The title compound is prepared according to the method of Example 19 using 2-hydroxymethyl-(5-methythio)thiophene instead of 2-hydroxymethylthiophene.

EXAMPLE 41

Preparation of N-hydroxy-N-[2-(3-thiomethoxythien-2-ylmethoxy)ethyl] urea

2-Hydroxymethyl-(3-methythio)thiophene is prepared by lithium aluminium hydride reduction of (3-methylthio)thiophene-2-carboxaldehyde. This aldehyde is obtained by reaction of methylmercaptan and 3-bromothiophene-2-carboxaldehyde. The title compound is prepared according to the method of Example 19 using 2-hydroxymethyl-(3-methythio)thiophene instead of 2-hydroxymethylthiophene.

EXAMPLE 42

Preparation of N-hydroxy-N-[2-(5-phenylthien-2-ylmethoxy)ethyl] urea

2-Hydroxymethyl-5-phenylthiophene is prepared by lithium aluminium hydride reduction of 5-phenylthiophene-2-carboxaldehyde. The title compound is prepared according to the method of Example 19 using 2-hydroxymethyl-5-phenylthiophene instead of 2-hydroxymethylthiophene.

EXAMPLE 43

Preparation of N-hydroxy-N-[2-(5-(4-chlorophenyl)thien-2-ylmethoxy)ethyl] urea

2-Hydroxymethyl-5-(4-chlorophenyl)thiophene is prepared by lithium aluminium hydride reduction of 5-(4-chloropenyl)thiophene-2-carboxaldehyde. The title compound is prepared according to the method of Example 19 using 2-hydroxymethyl-5-(4-chlorophenyl)thiophene instead of 2-hydroxymethylthiophene.

EXAMPLE 44

Preparation of N-hydroxy-N-[2-(5-(4-methylphenyl)thien-2-ylmethoxy)ethyl] urea

2-Hydroxymethyl-5-(4-methyphenyl)thiophene is prepared by lithium aluminium hydride reduction of 5-(4-methylphenyl)thiophene-2-carboxaldehyde. The title compound is prepared according to the method of Example 19 using 2-hydroxymethyl-5-(4-methyphenyl)-thiophene instead of 2-hydroxymethylthiophene.

EXAMPLE 45

Preparation of N-hydroxy-N-[2-(5-phenylfur-2-ylmethoxy)ethyl] urea

2-Hydroxymethyl-5-phenylfuran is prepared by lithium aluminium hydride reduction of 5-phenylfuran-2-carboxaldehyde. The title compound is prepared according to the method of Example 19 using 2-hydroxymethyl-5-phenylfuran instead of 2-hydroxymethylthiophene.

EXAMPLE 46

Preparation of N-hydroxy-N-[2-(5-(4-chlorophenyl)fur-2-ylmethoxy)ethyl] urea

2-Hydroxymethyl-5-(4-chlorophenyl)furan is prepared by lithium aluminium hydride reduction of 5-(4-chloropenyl)furan-2-carboxaldehyde. The title compound is prepared according to the method of Example 19 using 2-hydroxymethyl-5-(4-chlorophenyl)furan instead of 2-hydroxymethylthiophene.

EXAMPLE 47

Preparation of N-hydroxy-N-[2-(5-(4-methylphenyl)fur-2-ylmethoxy)ethyl] urea

2-Hydroxymethyl-5-(4-methyphenyl)furan is prepared by lithium aluminium hydride reduction of 5-(4-methylphenyl)furan-2-carboxaldehyde. The title hydroxy urea is prepared according to the method of Example 19 using 2-hydroxymethyl-5-(4-methyphenyl)-furan instead of 2-hydroxymethylthiophene.

EXAMPLE 48

Preparation of N-hydroxy-N-[2-(5-(2-phenylethenyl)thien-2-ylmethoxy)ethyl] urea

2-Hydroxymethyl-5-(trans 2-phenylethenyl)thiophene is prepared by lithium aluminium hydride reduction of 5-(trans 2-phenylethenyl)-thiophene-2-carboxaldehyde. The title compound is prepared according to the method of Example 19 using 2-hydroxymethyl-5-(trans 2-penylethenyl)thiophene instead of 2-hydroxymethylthiophene.

EXAMPLE 49

Preparation of N-hydroxy-N-[2-(5-(2-phenylethenyl)fur-2-ylmethoxy)ethyl] urea

2-Hydroxymethyl-5-(trans-2-phenylethenyl)furan is prepared by lithium aluminium hydride reduction of 5-(trans-2-phenylethenyl)-furan-2-carboxaldehyde. The title hydroxy urea is prepared according to the method of Example 19 using 2-hydroxymethyl-5-(trans 2- phenylethenyl)furan instead of 2-hydroxymethylthiophene.

EXAMPLE 50

Preparation of N-hydroxy-N-[2-(thieno[2,3-b]thien-2-ylmethoxy)ethyl] urea

2-Hydroxymethyl-thieno[2,3-b]thiophene is prepared by lithium aluminium hydride reduction of thieno[2,3-b]thiophene-2-carboxaldehyde. The title compound is prepared according to the method of Example 19 using 2-hydroxymethyl-thieno[2,3-b]thiophene instead of 2-hydroxymethylthiophene.

EXAMPLE 51

Preparation of N-hydroxy-N-[2-(thieno[3,2-b]thien-2-ylmethoxy)ethyl] urea

2-Hydroxymethyl-thieno[3,2-b]thiophene is prepared by lithium aluminium hydride reduction of thieno[3,2-b]thiophene-2-carboxaldehyde. The title hydroxy urea is prepared according to the method of Example 19 using 2-hydroxymethyl-thieno[3,2-b]thiophene instead of 2-hydroxymethylthiophene.

Lipoxygenase Inhibition Determination

Assays to determine 5-lipoxygenase inhibitory activity were performed in 200 mL incubations containing the 20,000 xg supernatant from 1.5 million homogenized RBL-1 cells and various concentrations of the test compound. Reactions were initiated by addition of radiolabeled arachidonic acid and terminated by acidification and ether extraction. Reaction products were separated from nonconverted substrate by thin layer chromatography and measured by liquid scintillation spectroscopy. All incubations are performed in triplicate. Inhibition of 5-lipoxygenase activity was calculated as the ratio of the amount of product formed in the presence and absence of inhibitor. $IC_{50}$ values (concentration of compound producing 50% enzyme inhibition) were calculated by linear regression analysis of percentage inhibition versus log inhibitor concentration plots. (Dyer, R. D.; Haviv, F.; Hanel, A. M.; Bornemier, D. A.; Carter, G. W. Fed. Proc., Fed. Am. Soc. Exp. Biol. 1984, 43, 1462A). Results for compounds of the foregoing examples are indicated in Table 1.

TABLE 1

In Vitro Inhibitory Potencies of Compounds of the Present Invention Against 5-Lipoxygenase from RBL-1 20,000 × g Supernatant

| Example | $IC_{50} \times 10^6$ Molar |
|---|---|
| 1 | 5.5 |
| 2 | 9.7 |
| 3 | 12 |
| 4 | 6.3 |
| 5 | 4.6 |
| 6 | 7.3 |
| 7 | 6.6 |
| 8 | 5.7 |
| 9 | 6.9 |
| 10 | 6.0 |
| 11 | 9.3 |
| 12 | 7.3 |
| 13 | 1.9 |
| 14 | 3.0 |
| 15 | 0.2 |
| 16 | 0.67 |
| 17 | 0.46 |
| 18 | 27.6 |
| 19 | 4.1 |

TABLE 1-continued

In Vitro Inhibitory Potencies of Compounds of the Present Invention Against 5-Lipoxygenase from RBL-1 20,000 × g Supernatant

| Example | $IC_{50} \times 10^6$ Molar |
|---|---|
| 20 | 4.5 |
| 21 | 8.4 |

Inhibition of Leukotriene Biosynthesis

Inhibition of the biosynthesis of leukotrienes in vivo after oral administration of compound was determined using a rat peritoneal anaphylaxis model in a similar manner as that described by Young and coworkers (Young, P. R.; Dyer, R. D.; Carter, G. W. Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antigen antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group, and the results are presented in Table 2 for representative compounds of the present invention.

TABLE 2

Inhibition of Leukotriene Biosynthesis

| Example | Percent Inhibition of Leukotrienes at 200 μmol/kg (Oral Dose) |
|---|---|
| 1 | 71 |
| 3 | 77 |
| 10 | 75 |
| 11 | 78 |
| 14 | 92 |
| 17 | 89 |
| 19 | 100 |

We claim:
1. A compound of the formula

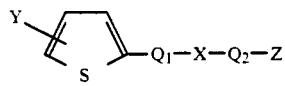

or a pharmaceutically acceptable salt thereof wherein
X is oxygen or sulfur;
Y is one or two substituents independently selected from the group consisting of
hydrogen,
hydroxy,
halogen,
cyano,
alkyl of from one to six carbon atoms,
halogenated alkyl of from one to six carbon atoms,
alkoxy of from one to six carbon atoms,
alkylthio of from one to six carbon atoms,
alkoxy(carbocyclic aryl) in which the alkoxy portion contains from one to six carbon atoms,
alkylthio(carbocyclic aryl) in which the alkylthio portion contains from one to six carbon atoms,
(carbocyclic aryl)alkoxy in which the alkoxy portion contains from one to six carbon atoms, (carbocyclic aryl)alkylthio in which the alkylthio portion contains from one to six carbon atoms,
(carbocyclic aryl)oxy,
(carbocyclic aryl)thio,
alkylamido of from one to six carbon atoms,
cycloalkyl of from three to eight carbon atoms,
alkanoyl of from one to six carbon atoms,
alkoxycarbonyl,
amino,
alkylamino of from one to six carbon atoms,
dialkylamino in which the two alkyl groups are independently selected from the group consisting of alkyl of from one to six carbon atoms,
—CRROR, —NRC(O)R, —NRC(O)OR, and —C(O)NRR wherein R, at each occurrence, is independently selected from hydrogen and alkyl of from one to six carbon atoms;
$Q_1$ is divalent alkylene of from one to six carbon atoms;
$Q_2$ is divalent alkylene from two to ten carbon atoms; and
Z is $N(OR_1)COR_2$ wherein
$R_1$ is selected from hydrogen or a pharmaceutically suitable salt, and
$R_2$ is selected from the group consisting of
amino,
alkylamino of from one to six carbon atoms in which the alkyl group is optionally substituted by
hydroxyl,
halogen,
alkoxy, or
carboxyl,
dialkylamino in which the alkyl groups are independently selected from one to six carbon atoms and in which the alkyl groups are optionally independently substituted by
hydroxyl,
halogen,
alkoxy, or
carboxyl,
cycloalkylamino of from three to six carbon atoms, 2-hydroxyethylamino,
N-morpholino,
N-thiomorpholino,
N-piperazino,
N'-alkyl-N-piperazino, and
cyclopropylmethylamino.

2. A compound as defined by claim 1 or a pharmaceutically acceptable salt thereof wherein $R_2$ is selected from
amino,
alkylamino of from one to six carbon atoms in which the alkyl group is optionally substituted by
hydroxyl,
halogen,
alkoxy, or
carboxyl, and
dialkylamino in which the alkyl groups are independently selected from one to six carbon atoms and in which the alkyl groups are optionally independently substituted by
hydroxyl,
halogen,
alkoxy, or
carboxyl.

3. A compound as defined by claim 1 wherein X is oxygen.

4. A compound as defined by claim 1 wherein X is sulfur.

5. A compound as defined by claim 1 selected from the group consisting of
N-Hydroxy-N-(2-(1-(5-methylthien-2-yl)methoxy)propyl) urea;
N-Hydroxy-N-(2-(1-(5-methylthien-2-yl)methoxy)ethyl) urea.
N-Hydroxy-N-(2-(thien-2-ylmethoxy)ethyl) urea;
N-Hydroxy-N-(2-(thien-2-ylmethoxy)propyl)urea;
N-Hydroxy-N-(2-(1-(thien-3-yl)methoxy)propyl) urea;
N-Hydroxy-N-(2-(thien-3-ylmethoxy)ethyl) urea.
N-Hydroxy-N-(2-(1-((5-tert butylthio)thien-2-yl)methoxy)ethyl)urea;
N-hydroxy-N-(2-(thien-2-ylmethoxy)ethyl)-N'-methyl urea;
N-hydroxy-N-(2-(thien-2-ylmethoxy)ethyl)-N'-butyl urea
N-hydroxy-N-(2-(thien-2-ylmethoxy)ethyl)-N'-benzyl urea;
N-hydroxy-N-(2-(thien-2-ylmethoxy)ethyl)-N'-phenyl urea;
N-hydroxy-N-(2-(thien-2-ylmethoxy)ethyl)-N'-hydroxyethyl urea;
N-hydroxy-N-(2-(thien-2-ylmethoxy)ethyl) N'-1-(4-carbomethoxyhexyl) urea;
N-hydroxy-N-(2-(thien-2-ylmethoxy)ethyl) N'N'-dimethyl urea
N-hydroxy-N-(2-(thien-2-ylmethoxy)ethyl) N'-morpholinyl urea;
N-hydroxy-N-(2-(thien-2-ylmethoxy)ethyl) N'-(N''-methyl)piperazinyl urea;
N-hydroxy-N-(2-(5-(phenylthio)thien-2-ylmethoxy)ethyl) urea
N-hydroxy-N-(2-(5-(4-chlorophenylthio)thien-2-ylmethoxy)ethyl) urea;
N-hydroxy-N-(2-(3-(phenylthio)thien-2-ylmethoxy)ethyl) urea;
N-hydroxy-N-(2-(3-(4-bromophenylthio)thien-2-ylmethoxy)ethyl) urea;
N-hydroxy-N-(2-(5-thiomethoxythien-2-ylmethoxy)ethyl) urea
N-hydroxy-N-(2-(3-thiomethoxythien-2-ylmethoxy)ethyl) urea;
N-hydroxy-N-(2-(5-phenylthien-2-ylmethoxy)ethyl) urea
N-hydroxy-N-(2-(5-(4-chlorophenyl)thien-2-ylmethoxy)ethyl) urea;
N-hydroxy-N-(2-(5-(4-methylphenyl)thien-2-ylmethoxy)ethyl) urea;
N-hydroxy-N-(2-(5-(2-phenylethenyl)thien-2-ylmethoxy)ethyl) urea;
or a pharmaceutically acceptable salt thereof.

6. A pharmaceutical compositions for inhibiting lipoxygenase enzyme activity and leukotriene biosynthesis comprising a therapeutically effective amount of a compound as defined by claim 1 in combination with a pharmaceutically acceptable carrier.

7. A method of inhibiting 5-lipoxygenase activity in a mammal in need of such treatment comprising administering to a mammal in need of such treatment a therapeutically effective amount of a compound as defined by claim 1.

* * * * *